United States Patent [19]

Okano et al.

[11] 4,112,241
[45] Sep. 5, 1978

[54] PROCESS FOR PRODUCING ALKYLENE GLYCOL ESTERS

[75] Inventors: Takeshi Okano, Machida; Naoto Wada, Komae; Yoshimitsu Kobayashi, Tokyo, all of Japan

[73] Assignee: Mitsubishi Chemical Industries Limited, Tokyo, Japan

[21] Appl. No.: 783,226

[22] Filed: Mar. 30, 1977

Related U.S. Application Data

[63] Continuation-in-part of Ser. No. 704,743, Jul. 12, 1976, abandoned.

[30] Foreign Application Priority Data

| Jul. 31, 1975 | [JP] | Japan | 50-93468 |
| Jul. 31, 1975 | [JP] | Japan | 50-93469 |
| Sep. 2, 1975 | [JP] | Japan | 50-106137 |
| Dec. 25, 1975 | [JP] | Japan | 50-155192 |

[51] Int. Cl.² .................................................. C07C 67/05
[52] U.S. Cl. .................................. 560/246; 560/112; 260/410.6; 252/438
[58] Field of Search ............ 260/497 R, 497 A, 410.6; 560/112, 246

[56] References Cited

U.S. PATENT DOCUMENTS

| 3,349,118 | 10/1967 | Kohll | 260/497 A |
| 3,444,189 | 5/1966 | Olivier | 260/497 A |
| 3,542,857 | 11/1970 | Lutz | 260/497 R |
| 3,686,287 | 8/1972 | Knights | 260/497 A |
| 3,770,813 | 11/1973 | Kollar | 260/497 R |
| 3,859,336 | 1/1975 | Aguilo | 260/497 A |
| 4,000,185 | 12/1976 | Kurkov | 260/497 R |

FOREIGN PATENT DOCUMENTS

| 45-14774 | 5/1970 | Japan | 260/497 A |
| 45-32414 | 10/1970 | Japan | 260/497 A |
| 45-32415 | 10/1970 | Japan | 260/497 A |
| 52-17412 | 2/1977 | Japan | 260/497 A |
| 52-17414 | 2/1977 | Japan | 260/497 A |
| 52-31014 | 3/1977 | Japan | 260/497 A |

*Primary Examiner*—James O. Thomas, Jr.
*Assistant Examiner*—Michael Shippen
*Attorney, Agent, or Firm*—Oblon, Fisher, Spivak, McClelland & Maier

[57] ABSTRACT

Alkylene glycol esters are produced by the reaction of an olefin, a carboxylic acid and molecular oxygen employing an iodine-containing substance and a nitrogen oxide as a catalyst.

11 Claims, No Drawings

PROCESS FOR PRODUCING ALKYLENE GLYCOL ESTERS

CROSS-REFERENCE TO A RELATED APPLICATION

This application is a continuation-in-part of application Ser. No. 704,743 filed July 12, 1976, now abandoned.

BACKGROUND OF THE INVENTION

1. Field of the Invention

This invention relates to a process for producing alkylene glycol esters, e.g., ethylene glycol esters, and more particularly, to the oxidative acylation of olefins.

2. Description of the Prior Art

Alkylene glycol esters are useful as solvents and plasticizers. For example, ethylene glycol esters may be used as a solvent, or as an intermediate in the manufacture of ethylene glycol which is a commercially significant intermediate to polyethylene terephthalate.

A variety of catalysts are known to be useful for the production of alkylene glycol esters by the reaction of olefins, carboxylic acids and molecular oxygen.

U.S. Pat. No. 3,770,813 to Kollar, issued Nov. 6, 1973 discloses a process employing a catalyst system consisting of iodine (or an iodine producing compound and oxygen) and at least one cation selected from the group consisting of alkali metal cations, a heavy metal cation of atomic number 21–30 and 48, and nitrogen-containing cations derived from tri-lower alkyl amines, ammonia, piperidine or pyridine. The drawback of this process is relatively low reaction rates which require the use of high reaction temperatures in the range of 130° to 160° C, and relatively higher reaction pressures.

U.S. Pat. No. 3,689,535 to Kollar, issued Sept. 5, 1972, discloses a process which involves the use of a catalyst system consisting of bromine or chlorine (or a bromine or chlorine containing compound) and a variable valence metal cation such as Ce, Mn, Sb, V, Ga, As, Cr, Cu, Ag and Co. This process suffers from relatively low reaction rates which require the use of high reaction temperatures in the range of 80° to 200° C. A further disadvantage of this process is the corrosion problem associated with the corrosive nature of this catalyst system at high temperatures.

U.S. Pat. No. 2,519,754 to Gresham et al, issued Aug. 22, 1950, discloses the use of hydrogen halides (preferably hydrobromic acid) or organic halides (preferably aliphatic bromides) as a catalyst. However, this process requires the use of high reaction temperatures in the range of 180° C to 220° C.

U.S. Pat. No. 3,427,348 to Olson, issued Feb. 11, 1969 discloses a catalyst system consisting of selenium dioxide and a mineral acid. The disadvantage of this catalyst system is relatively low selectivity.

U.S. Pat. No. 3,778,468 to Kollar, issued Dec. 11, 1973, discloses a process for the production of ethylene glycol esters employing a catalyst comprising cationic selenium and at least one halogenated substance selected from the group consisting of elemental bromine, elemental chlorine, a bromide-producing compound and a chloride-producing compound.

U.S. Pat. No. 3,668,239 to Kollar, issued June 6, 1972, discloses a catalyst system consisting of tellurium and an appropriate bromine source.

U.S. Pat. No. 3,479,395 to Huguet, issued Nov. 18, 1969, discloses a catalyst system consisting of tellurium dioxide, an alkali metal halide and a redox system.

U.S. Pat. No. 2,497,408 to Gresham, issued Feb. 14, 1950, discloses a process for the manufacture of propylene glycol esters employing a mixed catalyst of a metal acetate such as lead acetate or ferric acetate and an alkaline earth metal acetate.

U.S. Pat. No. 3,299,110 to Pine, issued Jan. 17, 1967, discloses a molybdenum-containing catalyst such as molybdenum sulfide, molybdenum oxide and sulfided cobalt molybdate.

British Pat. No. 1,058,995 discloses a catalyst system consisting of palladium II salt, metal acetate such as alkali metal, alkaline earth metal, cupric, ferric, stannic and nickel acetates, and a metal halide selected from alkali metal, alkaline earth metal, cupric, ferric, stannic and nickel chlorides and bromides.

British Pat. No. 1,124,862 discloses a catalyst system consisting of a palladous salt and a nitrogen oxide such as a nitrate or nitrite of a metal of Group I, II or VIII of the Periodic Table, nitric acid, nitrous acid, NO, $NO_2$, $N_2O_5$ or $N_2O_3$.

U.S. Pat. No. 3,262,969 to Clark et al, issued July 26, 1966, discloses a catalyst system consisting of a palladous salt, a salt of a carboxylic acid, an alkali metal halide and a redox system.

U.S. Pat. No. 3,349,118 to Kohll et al., issued Oct. 24, 1967, discloses a catalyst system consisting of palladium halides (preferably chloride) and nitric acid.

U.S. Pat. No. 3,859,336 to Aguilo et al., issued Jan. 7, 1975, discloses a catalyst system consisting of noble metal halides and nitrogen oxides such as nitric acid, nitric oxide and nitrogen dioxide. It also discloses that the halogens of the noble metal halides are preferred in order of decreasing atomic weight.

However, the processes employing a noble metal salt as a main catalyst pose the disadvantages such as a loss of the expensive noble metal salt during the operation, plugging of the system caused by the deposit of the noble metal, and relatively low selectivity caused by the formation of unwanted by-products such as aldehydes and ketones. There is a need, therefore, for a more efficient, selective and inexpensive process for the production of alkylene glycol esters from olefins and carboxylic acids.

SUMMARY OF THE INVENTION

Accordingly, it is an object of this invention to provide a commercially practical process for producing alkylene glycol esters in high yields and selectivities. Briefly, this and other objects of this invention, as will hereinafter become clear from the ensuing discussion, have been attained by reacting an olefin, a carboxylic acid and molecular weight employing as a catalyst an iodine-containing substance selected from the group consisting of iodine and iodine-containing compounds, and a nitrogen oxide.

DESCRIPTION OF THE PREFERRED EMBODIMENTS

The method of this invention is illustrated by the following chemical equations:

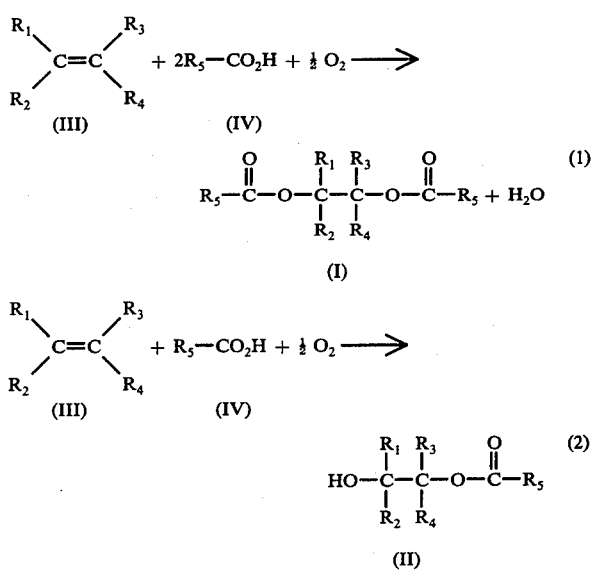

In the above formulas, $R_1$, $R_2$, $R_3$ and $R_4$ are selected from the group consisting of hydrogen, alkyl of 1-20 (preferably 1-10) carbon atoms and aryl of 6-10) carbon atoms; and $R_5$ is alkyl of 1-20 (preferably 1-10) carbon atoms or aryl of 6-20 (preferably 6-10) carbon atoms. The above-described alkyl or aryl may be substituted with reaction-inert substituents such as halo, nitro, alkoxy, alkoxycarbonyl, carbonyl and the like.

Suitable olefins (III) for use in the present process include stright-chain olefins such as ethylene, propylene, 1-butene, 2-butene, 1-hexene, 1-octene, 1-decene and the like; and branched-olefins such as isobutylene, 2-methyl-1-pentene, 2-methyl-1-butene and the like. Preferred olefins are ethylene and propylene.

Suitable carboxylic acids (IV) for use in the present process include aliphatic carboxylic acids such as acetic acid, monochloroacetic acid, propionic acid, butyric acid, valeric acid, isovaleric acid, octanoic acid, phenylacetic acid, phenylpropionic acid and the like; and aromatic carboxylic acids such as benzoic acid, toluic acid and the like. Preferred carboxylic acids are acetic acid, propionic acid and benzoic acid. Especially preferred is acetic acid. It is to be noted that when water is present in the reaction system in an amount sufficient to effect the hydrolysis of alkylene glycol diesters (I), alkylene glycol monoesters and alkylene glycols are obtained.

It is also to be noted that the presence of water favors the formation of alkylene glycols by the oxidative hydroxylation of olefins as well as by the hydrolysis of the alkylene glycol esters.

The characteristic feature of this invention is a new catalyst system comprising at least one iodine-containing substance selected from the group consisting of iodine and iodine containing compounds, and at least one nitrogen oxide. Another characteristic feature of this invention is that the reaction is carried out in the substantial absence of noble metals and salts thereof.

As used hereinabove, and as will be used hereinafter and in the claims, the term "a nitrogen oxide" is intended to include oxides of nitrogen such as NO, $NO_2$, $N_2O_3$, $N_2O_4$ and $N_2O_5$, nitrogen containing oxyacids such as nitrous acid, hyponitrous acid and nitric acid, and the salts of the oxyacids.

It is believed that an iodine containing substance acts as a catalyst while reversibly varying its oxidative number, and the iodine-containing substance is believed to be present in the reaction system in the form of $I^-$, $I_2$, $I_2O$, HIO, $R-CO_2I$ (wherein R is alkyl), $IO_3^-$, $I_2O_5$ or the like. Therefore, in addition to iodine, any iodine containing compound capable of affording in the reaction system a species of an iodine-containing substance which can reversibly vary its oxidation number may be introduced into the reaction system. Suitable iodine containing substances are iodine; hydroiodic acid; organic alkyl iodides of 1-10 carbon atoms, such as ethylene iodohydrin and ethylene diiodide; alkali metal salts of hydroiodic acid such as lithium iodide, sodium iodide and potassium iodide; alkaline earth metal salts of hydroiodic acid such as magnesium iodide; aluminum iodide; hypoiodous acid; alkali metal salts of hypoiodous acid such as lithium hypoiodite and sodium hypoiodite; alkaline earth metal salts of hypoiodous acid such as magnesium hypoiodite; aluminum hypoiodite; alkyl carbonyl hypoiodites ($RCO_2I$ wherein R is alkyl) of 2-10 carbon atoms such as methylcarbonyl hypoiodite; iodic acid; alkali metal salts of iodic acid such as lithium iodate and potassium iodate; alkaline earth metal salts of iodic acid such as magnesium iodate; aluminum iodate; peroxyiodic acid; alkali metal salts of peroxyiodic acid such as lithium periodate; alkaline earth metal salts of peroxyiodic acid such as magnesium periodate; aluminum peroxyiodate; $I_2O$; $I_2O_5$; polyiodic acid; alkali metal salts of polyiodic acid such as lithium polyiodide; alkaline earth metal salts of polyiodic acid such as magnesium polyiodide; and aluminum polyiodide.

The preferred iodine containing substances are iodine, hydroiodic acid, organic alkyl iodide of 1-10 carbon atoms and alkali metal salts of hydroiodic acid.

Especially preferred are iodine, hydroiodic acid, ethylene iodohydrin, ethylene diiodide and lithium iodide. The amount of the iodine-containing substance to be used is not critical, and is normally up to one gram equivalent per liter of the reaction solution.

It is also believed that a nitrogen oxide which is another essential component of the catalyst system of this invention acts as a catalyst, in a manner similar to that of the iodine-containing substance, while reversibly varying its oxidation number, and the nitrogen oxide is believed to be present in the reaction system in the form of $N_2O$, NO, $NO_2$, $N_2O_3$, $N_2O_4$, $N_2O_5$, $HNO_3$, $NO_2^-$, $NO_3^-$, alkyl nitrites (R-ONO wherein R is alkyl), alkyl carbonyl nitrites

wherein R is alkyl) or the like. Therefore, any nitrogen oxide capable of affording in the reaction system a species of a nitrogen oxide which can reversibly vary its oxidation number may be introduced into the reaction system.

Suitable nitrogen oxides are nitric acid; alkali metal salts of nitric acid such as lithium nitrate, sodiun nitrate and potassium nitrate; alkaline earth metal salts of nitric acid such as magnesium nitrate; aluminum nitrate; NO; $NO_2$; $N_2O_3$; $N_2O_5$; nitrous acid; alkali metal salts of nitrous acid such as lithium nitrite and sodium nitrite; alkaline earth metal salts of nitrous acid such as magnesium nitrite; aluninum nitrite; alkyl esters of nitrous acid having 1-10 carbon atoms such as ethyl nitrite; and alkyl esters of nitric acid having 1-10 carbon atoms such as ethyl nitrate, ethylene dinitrate. The preferred nitrogen oxides are nitric acid, alkali metal salts of nitric acid and NO₂.

Especially preferred are nitric acid, lithium nitrate and NO₂.

The amount of the nitrogen oxide to be used is not critical, and is generally up to one mole per liter of the reaction solution.

The process of this invention can be carried out by introducing into the reactor in addition to the above-described catalyst system a promoter selected from the group consisting of substances consisting only of carbon and an element selected from the group consisting of lithium, beryllium, boron, sodium, magnesium, aluminum, silicon, potassium, calcium, scandium, titanium, vanadium, chromium, manganese, iron, cobalt, nickel, copper, zinc, germanium, gallium, zirconium, niobium, molybdenum, technetium, cadmium, indium, tin, antimony, tellurium, barium, cerium, hafnium, tantalum, tungsten, mercury, thallium, lead, bismuth and compounds thereof.

The preferred promoters are carbon, and an element selected from the group consisting of lithium, boron, sodium, aluminum, silicon, potassium, vanadium, iron, cobalt, nickel, copper, zinc, zirconium, molybdenum, tellurium, tungsten, lead, bismuth and compounds thereof.

Especially preferred are carbon, and an element selected from the group consisting of boron, iron, cobalt, nickel, zirconium and compounds thereof.

The addition of the promoter accelerates the reaction without lowering the selectivity.

The carbon single substance is generally called activated carbon including microcrystalline carbon and graphite. There is no particular limitation on the raw material and the activation method of the carbon. There is no stringent limitation on the content of trace components and the crystal structure of the activated carbon, and therefore, commercially available activated carbon can be used. Likewise, there is no especially strict limitation on a preparation method and physical properties of the graphite.

There is no particular limitation on the shape of the graphite, and the powdery or granular graphite having a suitable particle size can be used.

The above-described elements are added either in the form of single substance or in the form of compounds. There is no particular limitation on the form of the compounds, and they may be added in the form of oxides, sulfides, acids or bases which contains the above element, salts or the like. It is a characteristic feature of this invention that the results of the reaction are not quite affected by the fact whether the promoter is soluble or not.

The amount of the promoter to be used varies widely with the reaction temperature, the nature of the promoter, the amount of the catalyst, etc. Advantageously, only small amounts of the promoter, e.g., $10^{31}$ to $10^{-1}$ m mol per liter of the reaction solution, are needed for the successful operation of the process but larger amounts, e.g., up to one mole per liter of the reaction solution can also be used. The reaction mechanism for the process of this invention whereby alkylene glycol esters are obtained by the oxidative acylation of olefins is not fully understood. However, the following mechanism is possible.

Oxidation of a nitrogen oxide with an oxidizing agent, e.g., molecular oxygen converts the nitrogen oxide to its oxidized form which then oxidizes a reduced form of an iodine-containing substance, e.g., iodide ion, being present in the system, to give its oxidized form, e.g., $I_2$, $I_2O$, $IO^-$, $IO_2^-$, whereby the nitrogen oxide becomes reduced to its initial valence state. The oxidized form of the iodine-containing substance being formed, alone, or with the aid of a carboxylic acid or the like, oxidizes an olefin to give an alkylene glycol ester, whereby the iodine-containing substance becomes reduced to its initial valence state. While repeating the above-described reaction as one cycle, the chain response proceeds.

It follows from the above that the only requirement for the nitrogen oxide and the iodine-containing substance used in the process of this invention is that they be capable of undergoing alternative oxidation and reduction under the reaction conditions.

Therefore, any nitrogen oxide and iodine-containing substance each capable of undergoing alternative oxidation and reduction in the reaction system can be used regardless of their initial valence state.

The role of the promoter is not fully understood. However, it is believed that the promoter accelerates the oxidation of the reduced forms of the nitrogen oxide and the iodine-containing substance.

As stated above, the oxidizing agent employed in the process of this invention oxidizes the nitrogen oxide from a lower valence state to a higher valence state. In general, molecular oxygen is used as an oxidizing agent.

However, it goes without saying that, in place of molecular oxygen, an oxidizing agent capable of oxidizing nitrogen oxides, such as hydrogen peroxide, organic peroxides, persulfates, bromine, chlorine, ozone or the like can be used. In order for the process of this invention to be economically advantageous, it is preferred to use molecular oxygen as an oxidizing agent. Oxygen may be introduced into the reaction mixture as a stream of the substantially pure gas. Alternatively, it may be introduced as air or as a mixture of oxygen with an inert gas such as nitrogen.

In general, the reaction is carried out in the presence of a solvent. Examples of such solvents are the olefin starting materials, the carboxylic acid starting materials, the alkylene glycol ester products, glycols and a mixture thereof. Preferably, the carboxylic acid is used as a solvent as well as the source of the acid moiety of the desired ester.

In a continuous process, it is preferred that the glycol and its ester be separated from the reaction liquid, whereas the unreacted carboxylic acid and olefin be recovered for reuse. If desired, organic or inorganic solvents which are substantially inert to the reaction may be used as a solvent or a portion of the solvent. For example, when the reaction is carried out employing ethylene as an olefin, acetic acid as a carboxylic acid and the same amount of water as that of acetic acid as a solvent, the reaction rate and the selectivity are nearly equal to those obtained when water is not added, and the main products are ethylene glycol monoacetate and ethylene glycol diacetate.

When water is added in an amount larger than that of acetic acid, ethylene glycol is formed as a by-product. However, the formation of glycols is not a hindrance to commercial development of the process of this invention, because the glycols find wide uses.

In order to obtain the desired products of this invention which are ethylene glycol monoacetate and ethylene glycol diacetate in high selectivity, it is preferred that the water content of the solution be not more than 20 percent by weight. In order to obtain ethylene glycol diacetate in high selectivity, it is preferred that the water content of the solution be not more than 5 percent by weight.

The reaction temperature is not critical in the present invention except to retain a liquid phase. The lower the temperature, the lower is the reaction rate. On the other hand, the higher the temperature, the lower is the solubility of the gaseous starting materials (olefins, oxygen, iodine containing substances and nitrogen oxides) in the reaction mixture.

Accordingly, the preferred reaction temperature is in the range of from room temperature to 200° C. The reaction pressure is not an important variable and any pressure sufficient to maintain a liquid phase at the temperature being used is satisfactory. The reaction rate becomes higher as the reaction pressure increases. However, the high reaction pressure requires the use of a costly high pressure reactor. Accordingly, the preferred reaction pressure is generally in the range of from atmospheric pressure to about 50 Kg/cm$^2$.

The reaction is carried out in any suitable apparatus, e.g., fixed bed, slurry-type and moving bed reactor, and can be done batchwise or continuously.

In general, the carboxylic acid is added in liquid form. In a continuous process, the unreacted carboxylic acid, after leaving the reactor, is separated from the reaction mixture for reuse.

The gaseous olefin is introduced alone or in combination with molecular oxygen into the reactor. The liquid or solid olefin is introduced into the reactor alone or as a solution by dissolving it in a reaction medium, or as a gas by gasifying it in a vaporizer. The unreacted olefin, after leaving the reactor, is separated from the reaction products for reuse.

The iodine-containing substance and the nitrogen oxide are separated from the reaction products, and can be reused after being subjected to a suitable operation for regeneration, e.g., reoxidation, if necessary.

The promoter which is completely dissolved in the reaction system can be recycled into the system along with the iodine-containing substance and the nitrogen oxide.

The promoter which is suspended in the reaction system can be kept in the system by placing a filter at the liquid exit from the reactor, or can be recycled into the system by removing a portion of the reaction liquid from the reactor and then recovering it by filtration followed by being subjected to a suitable operation for regeneration, if necessary.

The promoter which is insoluble in the reaction system can be used as a fixed bed or fluidized system such as a slurry dispersion. Typical supports for fixed bed systems include kieselguhr, silicon carbide and titania.

Having generally described this invention, a more complete understanding can be obtained by reference to certain examples and reference examples which are provided herein for purposes of illustration only and are not intended to be limiting in any manner.

In the following examples and reference examples, the products, the conversion and the selectivity were investigated by gas chromatographic analysis.

EXAMPLE 1

To a 100 ml round botton flask fitted with an agitator, a reflux condenser, a gas inlet tube and a thermometer were added 2 g (15 millimoles) of lithium iodide, 0.69 g (10 millimoles) of lithium nitrate and 80 ml of acetic acid. The flask was set up in a bath maintained at 80° C. A gas mixture comprising oxygen, nitrogen and ethylene was fed in the proportions by volume of 0.8 O$_2$/7.2 N$_2$/1.2 ethylene through the reaction mixture at a rate of 1.15 standard liters per hour with continuous stirring of the reaction mixture.

At the conclusion of the one hour reaction period, the conversion of ethylene was 50%. Analysis showed the formation of ethylene glycol monoacetate (hereinafter referred to as "EGMA") and ethylene glycol diacetate (hereinafter referred to as "EGDA") as the products. The combined yields of EGDA and EGMA based on the reacted ethylene were 95%. Small amounts of ethylidene diacetate (hereinafter referred to as "EDA") and acetaldehyde (hereinafter referred to as AcH) were obtained as by-products. At the end of the 5 hours reaction period, the conversion of ethylene and the selectivity of the products were not varied.

EXAMPLE 2

Employing 1 ml of nitric acid in place of lithium nitrate, Example 1 was repeated. At the conclusion of the one hour reaction period, the conversion of ethylene was 30%. The combined yields of EGDA and EGMA based on the reacted ethylene was 95%.

EXAMPLE 3

To a reactor similar to that described in Example 1 were added 3.3 g (20 millimoles) of potassium iodide, 1 ml (10 millimoles) of nitric acid and 80 ml of acetic acid. The flask was set up in a bath maintained at 80° C. A gas mixture comprising by volume 8.5% of oxygen, 80% of nitrogen and 11.5% of ethylene was fed through the reaction mixture at a rate of 1.15 standard liters per hour with continuous stirring of the reaction mixture. At the conclusion of the one hour reaction period, the conversion of ethylene was 45%, and the combined selectivities of the reacted ethylene to EGDA, EGMA and 2-iodoethyl acetate (hereinafter referred to as "IEA") were 95%.

EXAMPLE 4

To a reactor similar to that described in Example 1 was added 2.7 g (20 millimoles) of lithium iodide and 80 ml of acetic acid. The flask was set up in an oil bath maintained at 80° C. A gas mixture comprising by volume 78% of nitrogen, 11.2% of oxygen, 9.8% of ethylene and 1.0% of nitrogen dioxide was fed through the reaction mixture at a rate of 1.9 standard liters per hour with stirring of the reaction mixture. The reaction between ethylene and oxygen occurred about 3.5 hours after initiating the introduction of the gas mixture, and wad continued for 8 hours, at the end of which time the conversions per pass of ethylene and oxygen were 22% and 10% respectively.

The total amount of nitrogen dioxide which was fed into the reactor during the 8 hours reaction period was about 6.7 millimoles. The combined amounts of EGMA, EGDA and IEA which were formed in the 8 hours reaction period were 17 millimoles.

EXAMPLE 5

A 300 ml titanium-lined autoclave, fitted with a stirring apparatus, a gas inlet tube, a liquid inlet tube, a gas exit tube through a reflux condenser, and a liquid exit tube, was charged with 8.0 g (0.060 mole) of lithium iodide, 1.4g (0.020 mole) of lithium nitrate and 140 ml of acetic acid, and then pressurized to a pressure of 20 Kg/cm² gauge with a gas mixture comprising by volume 88% of nitrogen, 4% of oxygen and 8% of ethylene. The reactor was heated gradually to 127° C with stirring and maintained at this temperature, while feeding the gas mixture into the reactor at a rate of 36 standard liters per hour. A solution of 1 ml of nitric acid dissolved in 20 ml of acetic acid was pumped into the reactor with the use of a micro-pump. After the addition of nitric acid, the reaction mixture was withdrawn from the reactor via the liquid exit pipe at a rate of 20 ml per hour, and an amount of nitric acid was added to the recovered reaction mixture to provide a volume ratio of nitric acid to the recovered reaction mixture of 1:20, and then the recovered reaction mixture containing nitric acid was recycled to the reactor with the use of a micro-pump at a rate of 21 ml per hour.

The reaction was carried out continuously under the abovedescribed conditions, and steady-state was reached 2 hours after initiating the introduction of the gas mixture, and then the reaction was continued for an additional 5 hours, during which time average conversions of both ethylene and oxygen were 45%. At the end of 7.5 hours from the time of initiating the introduction of the gas mixture, the addition of nitric acid was terminated, and then the conversions of ethylene and oxygen decreased suddenly and fell to about 0% in the subsequent 2 hours.

The total amounts of EGMA and EGDA formed in the 9.5 hours reaction period were 0.42 mole.

EXAMPLE 6

The reactor, as described in Example 5, was charged with 8.5 g (0.060 mole) of 1,2-diiodoethane, 1.4 g (0.020 mole) of lithium nitrate and 160 ml of acetic acid.

The reaction was carried out in the same manner as in Example 5, with the exception that a flow rate of the gas mixture was 15 standard liters per hour, and that nitric acid was not added to the recycled reaction mixture.

The reaction occurred one hour after initiating the introduction of the gas mixture, at which time the conversions per pass of ethylene and oxygen were 33% and 52% respectively. At the end of 3 hours from the time of initiating the introduction of the gas mixture, the conversions per pass of ethylene and oxygen were 74% and 83% respectively.

EXAMPLE 7

To a reactor similar to that described in Example 1 were added 3.3 g (20 millimoles) of potassium iodide, 1 ml (10 millimoles) of nitric acid, 0.5 g of activated carbon prepared from coconut shells (manufactured by Dai-ichi Carbon Industries Company) and 80 ml of acetic acid. The flask was set up in an oil bath maintained at 65° C. A gas mixture comprising by volume 8.5% of oxygen, 80% of nitrogen and 11.5% of ethylene was fed through the reaction mixture at a rate of 1.15 standard liters per hour with continuous stirring of the reaction mixture. At the conclusion of the one hour reaction period, the conversion of ethylene was 90%. The combined yields of EGDA and EGMA were 95% based on the reacted ethylene. Trace amounts of EDA and AcH were detected as by-products.

EXAMPLE 8

Employing 0.75 g (5 millimoles) of sodium iodide in place of potassium iodide, Example 7 was repeated. At the conclusion of the one hour reaction period, the conversion of ethylene was 80%, and the combined yields of EGDA and EGMA were 95% based on the reacted ethylene.

EXAMPLE 9

Employing 0.5 g of powdery graphite (manufactured by Kanto Chemical Company) in place of activated carbon, Example 7 was repeated. At the end of the one hour reaction period, the conversion of ethylene was 86% and the combined yields of EGDA and EGMA were 95% based on the reacted ethylene.

EXAMPLE 10

To a reactor similar to that described in Example 1 were added 2.0 g (15 millimoles) of lithium iodide, 1 ml (10 millimoles) of nitric acid, 1.8 g (10 millimoles) of vanadium pentoxide and 80 ml of acetic acid. The flask was set up in an oil bath maintained at 80° C. A gas mixture comprising by volume 80% of nitrogen, 8.5% of oxygen and 11.5% of ethylene was fed through the reaction mixture at a rate of 1.15 standard liters per hour with stirring of the reaction mixture. At the end of the one hour reaction period, the conversion of ethylene was 90%. Analysis showed the formation of EGDA, EGMA and IEA. The selectivity of the reacted ethylene to EGDA, EGMA and IEA was above 95%.

EXAMPLE 11-25

To a reactor similar to that described in Example 1 were added 2 g (15 millimoles) of lithium iodide or 3.3 g (20 millimoles) of potassium iodide as an iodine source, 1 ml (10 millimoles) of nitric acid as a nitrogen oxide, 80 ml of acetic acid and a promoter indicated in the following table. A gas mixture was passed through the reaction mixture in the same manner as in Example 20, while maintaining the reaction temperature at 80° C. However, when the promoter was a nitrate, nitric acid was not added. At the conclusion of the one hour reaction period, the conversion of ethylene in each reaction was between 55 and 99%. The selectivity of the reacted ethylene to EGDA, EGMA and IEA was more than 95%. A trace amount of EDA was detected. The results are summarized in the following table.

| Example No. | Iodide | Promotor, Amount (g) | | Conversion of Ethylene (after one hour) |
|---|---|---|---|---|
| 11 | LiI | TeO$_2$, | 1.6g | 85% |
| 12 | KI | Silica-Alumina, | 0.5 | 70 |
| 13 | KI | Na$_2$TeO$_3$, | 2.2 | 70 |
| 14 | KI | Pb(OAC)$_4$, | 4.3 | 70 |
| 15 | KI | MoO$_3$, | 1.5 | 55 |
| 16 | KI | H$_2$WO$_4$, | 2.5 | 70 |
| 17 | KI | Iron powder, | 0.55 | 80 |
| 18 | KI | FeCl$_3$, | 1.6 | 88 |
| 19 | KI | Ni(NO$_3$)$_2$ . 6H$_2$O, | 2.9 | 74 |
| 20 | KI | Co(NO$_3$)$_2$ . 6H$_2$O, | 2.9 | 90 |
| 21 | KI | ZnO, | 0.8 | 63 |
| 22 | KI | CuO, | 0.8 | 80 |
| 23 | KI | Bi(NO$_3$)$_3$ . 5H$_2$O, | 4.9 | 55 |
| 24 | KI | B$_2$O$_3$, | 0.7 | 99 |
| 25 | KI | ZrOCl$_2$ . 8H$_2$O, | 3.2 | 92 |

REFERENCE EXAMPLE 1

To a reaction flask the same as that described in Example 1 were added 4 g (30 millimoles) of lithium iodide and 80 ml of acetic acid. The reaction was carried out under the same conditions as those of Example 1. At the conclusion of the one hour reaction period, the conversion of ethylene was 1%.

REFERENCE EXAMPLE 2

To a reaction flask the same as that described in Example 1 were added 0.69 g (10 millimoles) of lithium iodide and 80 ml of acetic acid. The reaction was carried out under the same conditions as those of Example 1.

At the conclusion of the one hour reaction period, the conversion of ethylene was less than 1%.

REFERENCE EXAMPLE 3

Employing 1.66 g (10 millimoles) of potassium iodide, 2.45 g (10 millimoles of $Mn(CH_3CO_2)_2 \cdot 4H_2O$ and 80 ml of acetic acid, Example 3 was repeated. At the end of the one hour reaction period, the conversions per pass of both ethylene and oxygen were less than 1%. The addition of 1.27 g (5 millimoles) of iodine to the system did not increase the conversions of ethylene and oxygen.

REFERENCE EXAMPLE 4

Employing 1.66 g (10 millimoles) of potassium iodide, 2.32 g (10 millimoles) of $Fe(CH_3CO_2)_3$, and 80 ml of acetic acid, Example 3 was repeated. At the end of one hour reaction period, the conversions per pass of both ethylene and oxygen were less than 1%. The addition of 1.27 g (5 millimoles) of iodine did not increase the conversions of ethylene and oxygen.

REFERENCE EXAMPLE 4

Employing 2.54 g (10 millimoles) of iodine, 7.9 g (100 millimoles) of pyridine and 80 ml of acetic acid, Example 3 was repeated. At the end of the one hour reaction period, the conversions per pass of both ethylene and oxygen were less than 1%.

It can be seen from the comparison of the examples with the reference examples that the combination of the iodine-containing substance and the nitrogen oxide increases the yields of the acetates of ethylene glycol considerably as compared to the use of the iodine-containing substance or the nitrogen oxide alone.

Having now fully described the invention, it will be apparent to one of ordinary skill in the art that many changes and modifications can be made thereto without departing from the spirit or scope of the invention as set forth herein.

What is claimed as new and intended to be covered by letters patent of the United States:

1. In a process for the production of alkylene glycol esters having the formula (I):

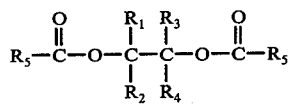

wherein $R_1$, $R_2$, $R_3$ and $R_4$ are selected from the group consisting of hydrogen, $C_1$-$C_{20}$ alkyl and $C_6$-$C_{20}$ aryl; and $R_5$ is $C_1$-$C_{20}$ alkyl or $C_6$-$C_{20}$ aryl, and/or the formula (II):

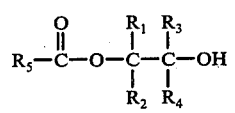

wherein $R_1$, $R_2$, $R_3$, $R_4$ and $R_5$ are as defined herein above, which comprises reacting an olefin having the formula (III):

wherein $R_1$, $R_2$, $R_3$ and $R_4$ are as defined herein above, a carboxylic acid having the formula (IV):

wherein $R_5$ is as defined herein above,
and molecular oxygen in the liquid phase, the improvement which comprises conducting said reaction in the presence of a catalyst of at least one nitrogen oxide selected from the group consisting of nitric acid, alkali metal salts of nitric acid, alkaline earth metal salts of nitric acid, aluminum nitrate, NO, $NO_2$, $N_2O_3$, $N_2O_5$ nitrous acid, alkali metal salts of nitrous acid, alkaline earth metal salts of nitrous acid, aluminum nitrite, alkyl esters of nitrous acid and alkyl esters of nitric acid in combination with at least one iodine-containing substance selected from the group consisting of iodine, hydroiodic acid, organic alkyl iodides, alkali metal salts of hydroiodic acid, alkaline earth metal salts of hydroiodic acids, aluminum iodide, hypoiodous acid, alkali metal salts of hypoiodous acid, alkaline earth metal salts of hypoiodous acid, aluminum hypoiodite, alkyl carbonyl hypoiodites, iodic acid, alkali metal salts of iodic acid, alkaline earth metal salts of iodic acid, aluminum iodate, peroxyiodic acid, alkali metal satls of peroxyiodic acid, alkaline earth metal salts of peroxyiodic acid, aluminum peroxyiodate, $I_2O$, $I_2O_5$, polyiodic acid, alkali metal salts of polyiodic acid, alkaline earth metal salts of polyiodic acid and aluminum polyiodate.

2. The process of claim 1, wherein $R_1$, $R_2$, $R_3$ and R are selected from the group consisting of hydrogen, $C_1$-$C_{10}$ alkyl and $C_6$-$C_{10}$ aryl; and $R_5$ is $C_1$-$C_{10}$ alkyl or $C_6$-$C_{10}$ aryl.

3. The process of claim 2, wherein the olefin is ethylene or propylene, and the carboxylic acid is acetic acid.

4. The process of claim 1, wherein the nitrogen oxide is selected from the group consisting of nitric acid, alkali metal salts of nitric acid and $NO_2$, and the iodine-containing substance is selected from the group consisting of iodine, hydroiodic acid, organic alkyl iodide of 1-10 carbon atoms and alkali metal salts of hydroiodic acid.

5. The process of claim 4, wherein the nitrogen oxide is nitric acid, lithium nitrate or $NO_2$, and the iodine-containing substance is iodine, hydroiodic acid, ethylene iodohydrin, ethylene diiodide or lithium iodide.

6. The process of claim 1, wherein the amount of the iodine-containing substance to be used is up to one gram equivalent per liter of the reaction solution.

7. The process of claim 1, wherein the amount of the nitrogen oxide to be used is up to one mole per liter of the reaction liquid.

8. The process of claim 1, wherein the reaction temperature is in the range of from room temperature to 200° C.

9. In a process for the production of alkylene glycol esters having the formula (I):

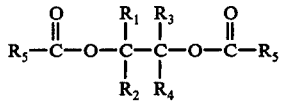

wherein $R_1$, $R_2$, $R_3$ and $R_4$ are selected from the group consisting of hydrogen, $C_1$-$C_{20}$ alkyl and $C_6$-$C_{20}$ aryl; and $R_5$ is $C_1$-$C_{20}$ alkyl or $C_6$-$C_{20}$ aryl, and/or the formula (II)

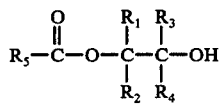

wherein $R_1$, $R_2$, $R_3$, $R_4$ and $R_5$ are as defined herein above, which comprises reacting an olefin having the formula (III):

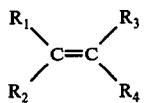

wherein $R_1$, $R_2$, $R_3$ and $R_4$ are as defined herein above, a carboxylic acid having the formula (IV):

wherein $R_5$ is as defined herein above, and molecular oxygen in the liquid phase, the improvement which comprises conducting said reaction in the presence of a catalyst of at least one nitrogen oxide selected from the group consisting of nitric acid, alkali metal salts of nitric acid, alkaline earth metal salts of nitric acid, aluminum nitrate, NO, $NO_2$, $N_2O_3$, $N_2O_5$, nitrous acid, alkali metal salts of nitrous acid, alkaline earth metal salts of nitrous acid, aluminum nitrite, alkyl esters of nitrous acid and alkyl esters of nitric acid in combination with at least one iodine-containing substance selected from the group consisting of iodine, hydroiodic acid, organic alkyl iodides, alkali metal salts of hydroiodic acid, alkaline earth metal salts of hydroiodic acid, aluminum iodide, hypoiodous acid, alkali metal salts of hypoiodous acid, alkaline earth metal salts of hypoiodous acid, aluminum hypoiodite, alkyl carbonyl hypoiodites, iodic acid, alkali metal salts of iodic acid, alkaline earth metal salts of iodic acid, aluminum iodate, peroxyiodic acid, alkali metal salts of peroxyiodic acid, alkaline earth metal salts of peroxyiodic acid, aluminum peroxyiodate, $I_2O$, $I_2O_5$, polyiodic acid, alkali metal salts of polyiodic acid, alkaline earth metal salts of polyiodic acid and aluminum polyiodate, and at least one promoter of carbon or a substance selected from the group consisting of elemental lithium, beryllium, boron, sodium, magnesium, aluminum, silicon, potassium, calcium, scandium, titanium, vanadium, chromium, manganese, iron, cobalt, nickel, copper, zinc, germanium, gallium, zirconium, niobium, molybdenum, technetium, cadmium, indium, tin, antimony, tellurium, barium, cerium, hafnium, tantalum, tungsten, mercury, thallium, lead, bismuth, and oxides, sulfides, acids, bases or salts of said elements.

10. The process of claim 9, wherein said substance is selected from the group consisting of lithium, boron, sodium, aluminum, silicon, potassium, vanadium, iron, cobalt, nickel, copper, zinc, zirconium, molybdenum, tellurium, tungsten, lead, bismuth and oxides, sulfides, acids, bases or salts thereof.

11. The process of claim 10, wherein said substance is selected from the group consisting of boron, iron, cobalt, nickel, zirconium and oxides, sulfides, acids, bases or salts thereof.

* * * * *